US00PP10884P

United States Patent [19]

Bradford et al.

[11] Patent Number: Plant 10,884

[45] Date of Patent: May 4, 1999

[54] NECTARINE TREE NAMED 'KAY SWEET'

[76] Inventors: Lowell Glen Bradford, 12439 E. Savana Rd.; Norman G. Bradford, 11875 E. Savana Rd., both of Le Grand, Calif. 95333

[21] Appl. No.: 08/975,100

[22] Filed: Nov. 20, 1997

[51] Int. Cl.[6] ..... A01H 5/00

[52] U.S. Cl. ..... Plt./190

[58] Field of Search ..... Plt./40.1, 41.1, Plt./41.2, 190, 187, 191

[56] References Cited

U.S. PATENT DOCUMENTS

P.P. 9,495 4/1996 Bradford et al. ..... Plt./41.1

*Primary Examiner*—Howard J. Locker

*Assistant Examiner*—Ashwin Mehta

[57] ABSTRACT

The present invention relates to a nectarine tree, Prunus persica, and more particularly to a new and distinct variety broadly characterized by a large size, vigorous, hardy, self-fertile, productive and regular bearing tree. The fruit matures under the ecological conditions described approximately the last week in May, with first picking on May 26, 1997. The fruit is uniformly medium in size, subacidic and very good in flavor, clingstone in type, firm in texture, and nearly full red in skin color. The variety was developed as an open pollinated seedling of an unnamed white flesh nectarine seedling.

1 Drawing Sheet

BACKGROUND OF THE VARIETY

In a continuing effort to improve the quality of shipping fruits, we, the inventors, typically hybridize a large number of nectarine, peach, plum, apricot, and cherry seedlings each year. We also grow a reasonable number of open pollinated seeds of each of these species. The present invention relates to a new and distinct variety of nectarine tree, which has been denominated varietally as 'Kay Sweet'. The present variety was selected from a group of open pollinated seedlings resulting from a mixed collection of seeds grown in 1992 from various unnamed white flesh nectarine trees located in a cultivated area of our experimental orchard at Bradford Farms near Le Grand, Calif. in Merced County (San Joaquin Valley). Subsequent to origination of the present variety of nectarine tree, we asexually reproduced it by budding and grafting, and such reproduction of plant and fruit characteristics were true to the original plant in all respects. The reproduction of the variety included the use of Nemaguard Rootstock, the standard of the stone fruit industry in central California, upon which the present variety was compatible and true to type.

The present variety is most similar to the 'Diamond Bright' U.S. Plant Pat. No. 9,495) nectarine by producing nearly full red colored clingstone nectarines that are yellow flesh in texture and that ripen in late May and early June, but is very distinguished therefrom and an improvement thereon by blooming early instead of late, as compared to other nectarine trees, and by producing fruit that is subacidic in flavor instead of acidic, that is much sweeter in flavor, and that is somewhat conical instead of globose in shape.

DRAWING

The accompanying photograph exhibits three whole fruits positioned to display the characteristics of the skin color and form, a sectioned half fruit divided transverse to the suture plane to reveal the flesh, a typical stone, and representative leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm eating ripe on Jun. 1, 1997. All major color code designations are by reference to the Inter-Society Color Council, National Bureau of Standards. Common color names are also used occasionally.

Tree

Size: Large, reaching a height of 11' [3.35 meters] after 5 growing seasons utilizing typical dormant pruning in the breeding grounds.

Vigor: Vigorous, responding favorably to irrigation and fertilization.

Growth: Spreading and dense.

Form: Vase formed.

Hardiness: Hardy, able to survive typical central California winters.

Production: Productive, thinning necessary.

Bearing: Regular bearer, with no alternate bearing yet observed.

Fertility: Self-fertile.

Trunk:

*Size.*—Medium, reaching a diameter of 5" [127 mm.] after the fifth growing season.

*Texture.*—Medium rough, with roughness increasing with age.

*Bark Color.*—Grayish brown [61. gy.Br].

*Lenticels.*—Numerous. Color: Moderate brown [58. m.Br]. Average size: 3/16" [4.8 mm.].

Branches:

*Size.*—Medium, typical of the species.

*Texture.*—Smooth on 1st year wood, increasing roughness with age.

*Color.*—1st Year wood topside: Grayish red [19. gy.R]. 1st Year wood underside: Brilliant yellow green [116. brill.YG]. Older wood: Dark grayish yellowish brown [81. d.gy.yBr].

*Lenticels.*—Numerous, small. Color: Moderate reddish brown [43. m.rBr]. Average size: 1/16" to 3/16" [1.6–4.8 mm.].

Leaves:
*Size.*—Medium. Average length: 5½" [139.7 mm.]. Average width: 1½" [38.1 mm.].
*Thickness.*—Medium.
*Form.*—Elliptical.
*Apex.*—Acuminate.
*Base.*—Acute.
*Surface.*—Smooth.
*Color.*—Dorsal surface: Moderate olive green [125. m.OlG]. Ventral surface: Moderate yellow green [120. m.YG].
*Margin.*—Finely serrate.
*Venation.*—Pinnately net veined.
*Petiole.*—Average length: ⅝" [15.9 mm.]. Average thickness: 1/16" [1.6 mm.]. Color: Moderate yellow green [120. m.YG].
*Stipules.*—Numerous, 2 per leaf, 4–6 per growing tip. Average length: 9/16" [14.3 mm.].
*Glands.*—Average number: 2–4 per leaf. Position: Alternately positioned on petiole and base of blade. Size: Small. Form: Reniform. Color: Moderate yellow green [120. m.YG].

Flower buds:
*Hardiness.*—Hardy, with respect to central California winters.
*Diameter.*—Typically ⅜" [9.5 mm.] 3 days before bloom.
*Length.*—Typically 13/16" [20.6 mm.] 3 days before bloom.
*Form.*—Free.
*Surface.*—Pubescent.

Flowers:
*Blooming period.*—Early as compared with other varieties.
*Onset of bloom.*—One percent on Feb. 17, 1997.
*Fragrance.*—Slight to moderate.
*Type.*—Showy.
*Average diameter.*—1⅞" [47.6 mm.].
*Color.*—Pale pink [7. p.Pk].

Fruit

Maturity when described: Hard ripe, Jun. 1, 1997.
Date of first picking: May 26, 1997.
Date of last picking: Jun. 6, 1997.
Size: Uniform, medium.
*Average diameter Axially.*—2⅜" [60.3 mm.].
*Average transversely in suture plane.*—2⅝" [66.7 mm.].
*Typical weight.*—5.63 ounces [160 grams].
Form: Uniform, somewhat oblong to conical, somewhat unsymmetrical.
*Longitudinal section form.*—Obovate.
*Transverse section through diameter.*—Round.
Suture: A sharp crease near the base transforming to a distinct shallow groove extending past the apex, having a marked depression beyond the pistil point.
Ventral surface: Slightly rounded, lipped throughout on one side.
Lips: Unequal.
Cavity: Flaring, rounded, circular, suture showing on one side, stem markings typical.
*Depth.*—½" [12.7 mm.].
*Breadth.*—¾" [19.1 mm.].
Base: Rounded to truncate.
Apex: Rounded to acute, with a few somewhat mammiform.
Pistil point: Apical, with some protruding beyond the suture.

Stem: Medium.
*Average length.*—⅜" [9.5 mm.].
*Average width.*—3/16" [4.8 mm.].

Skin:
*Thickness.*—Thin.
*Texture.*—Medium.
*Tenacity.*—Tenacious to flesh.
*Tendency to crack.*—Very slight in the wet season.
*Color.*—Dark red [16. d.R] over a deep reddish orange [36. deep rO] background with a few strong orange yellow [68. s.OY] freckles toward the apex.

Flesh:
*Color.*—Vivid yellow [82. v.Y] to the pit, with no red at the stone.
*Amygdalin.*—Scarce.
*Surface of pit cavity.*—Vivid yellow [82. v.Y] fibers breaking when twisted away from the stone.
*Juice.*—Abundant, rich.
*Texture.*—Firm, crisp.
*Fibers.*—Abundant, fine.
*Ripens.*—Slightly earliest at the apex.
*Flavor.*—Subacidic and mildly sweet averaging 15 brix.
*Aroma.*—Mild.
*Eating quality.*—Very good.

Stone

Type: Clingstone.
Form: Oval.
Base: Straight.
Apex: Acute to acuminate.
Sides: Equal.
Surface: Pitted toward the base, irregularly furrowed near the apex.
Ridges: Jagged toward the base.
Color: Light brown [57. l.Br] when first removed.
Pit wall: ¼" [6.4 mm.] thick.
Tendency to split: None observed.
Kernel:
*Form.*—Oval.
*Taste.*—Bitter.
*Viable.*—Yes.
*Average width.*—7/16" [11.1 mm.].
*Average length.*—11/16" [17.5 mm.].
*Color.*—Pale yellow [89. p.Y] when first removed, with moderate yellowish brown [77. m.yBr] veins.
*Pellicle color.*—Moderate yellowish brown [77. m.yBr].
*Amygdalin.*—Abundant.

Use

Market: Fresh and long distance shipping.
Keeping quality: Fruit quality observed to remain in good condition in excess of 14 days in cold room at 36° Fahrenheit [2° Celsius].
Resistance to insects: No unusual susceptibilities noted.
Resistance to diseases: No unusual susceptibilities noted.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, which is most similar to the 'Diamond Bright' (U.S. Plant Pat. No. 9,495) nectarine by producing nearly full red colored clingstone nectarines that are yellow flesh in texture and that ripen in late May and early June, but is very distinguished therefrom and an improvement thereon by blooming early instead of late, as compared to other nectarine trees, and by producing fruit that is subacidic in flavor instead of acidic, that is much sweeter in flavor, and that is somewhat conical instead of globose in shape.

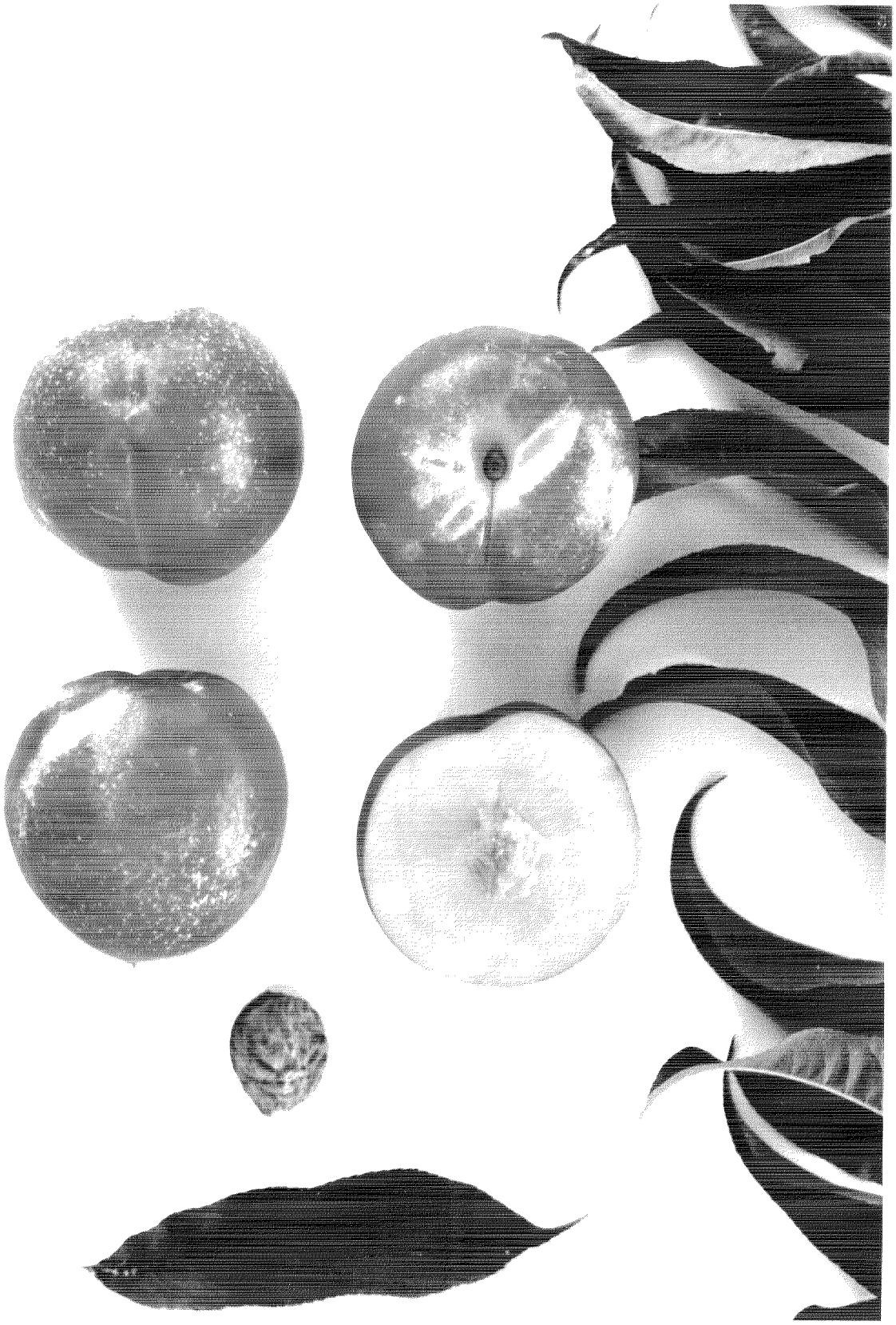

* * * * *